US012642866B2

(12) United States Patent
Balu-Iyer

(10) Patent No.: US 12,642,866 B2
(45) Date of Patent: Jun. 2, 2026

(54) COMPOSITION FOR IMMUNE TOLERANCE INDUCTION AND USE IN GENE THERAPY

(71) Applicant: The Research Foundation for The State University of New York, Amherst, NY (US)

(72) Inventor: Sathy V. Balu-Iyer, Amherst, NY (US)

(73) Assignee: The Research Foundation for The State University of New York, Amherst, NY (US)

( * ) Notice: Subject to any disclaimer, the term of this patent is extended or adjusted under 35 U.S.C. 154(b) by 240 days.

(21) Appl. No.: 18/261,829

(22) PCT Filed: Jan. 20, 2022

(86) PCT No.: PCT/US2022/013157
§ 371 (c)(1),
(2) Date: Jul. 17, 2023

(87) PCT Pub. No.: WO2022/159603
PCT Pub. Date: Jul. 28, 2022

(65) Prior Publication Data
US 2024/0082421 A1    Mar. 14, 2024

Related U.S. Application Data

(60) Provisional application No. 63/139,602, filed on Jan. 20, 2021.

(51) Int. Cl.
*A61K 9/127*    (2025.01)
*A61K 38/10*    (2006.01)
(Continued)

(52) U.S. Cl.
CPC .......... *A61K 47/6913* (2017.08); *A61K 38/10* (2013.01); *A61K 38/162* (2013.01);
(Continued)

(58) Field of Classification Search
None
See application file for complete search history.

(56) References Cited

U.S. PATENT DOCUMENTS

| | | |
|---|---|---|
| 2005/0191309 A1 | 9/2005 | Kakkis et al. |
| 2010/0104561 A1* | 4/2010 | Zhong .................. A61K 48/005 514/1.2 |
| 2019/0151426 A1* | 5/2019 | Balu-Iyer ............. A61K 31/436 |

FOREIGN PATENT DOCUMENTS

WO    2017176916 A1    10/2017

OTHER PUBLICATIONS

Mingozzi et al., "Overcoming Preexisting Humoral Immunity to AAV Using Capsid Decoys," Science Translational Medicine, Jul. 17, 2013, vol. 5, Issue 194.
(Continued)

*Primary Examiner* — Brian Gulledge
(74) *Attorney, Agent, or Firm* — Hodgson Russ LLP

(57) ABSTRACT

Provided are compositions and methods for reducing pre-existing antibodies against viral vector or gene-editing related proteins. The compositions showed reduction in various antibody titers by administration of a liposome composition complexed with a protein or fragment thereof of a viral vector. The liposomes comprise phosphatidylcholine and phosphatidylserine, wherein some or all of the PS is present as lyso-PS. The compositions and methods can be used in conjunction with gene therapy and nucleic acid based vector based vaccinations and therapeutics.

5 Claims, 7 Drawing Sheets

Specification includes a Sequence Listing.

Subcutaneous Induction Dosing | Oral Gavage Treatments | Sacrifice

Week 1-6    Week 7-15    16

Weekly Saphenous Sampling

(51) Int. Cl.

| | |
|---|---|
| *A61K 38/16* | (2006.01) |
| *A61K 39/00* | (2006.01) |
| *A61K 39/39* | (2006.01) |
| *A61K 47/24* | (2006.01) |
| *A61K 47/69* | (2017.01) |
| *A61P 37/06* | (2006.01) |

(52) U.S. Cl.

CPC .... *A61P 37/06* (2018.01); *A61K 2039/55555* (2013.01); *A61K 2039/577* (2013.01)

(56) References Cited

OTHER PUBLICATIONS

Velazquez et al., "Effective Depletion of Pre-existing Anti-AAV Antibodies Required Broad Immune Targeting," Molecular Therapy: Methods & Clinical Development, Mar. 4, 2017, pp. 159-168, vol. 4.

Mingozzi et al., "Overcoming the Host Immune Response to Adeno-Associated Virus Gene Delivery Vectors: The Race Between Clearence, Tolerance, Neutralization, and Escape," Annual Review of Virology, Sep. 29, 2017, pp. 511-534, vol. 4.

Long et al., "The Impact of Pre-existing Immunity on the Non-clinical Pharmacodynamics of AAV5-Based Gene Therapy," Molecular Therapy: Methods & Clinical Development, Jun. 2019, pp. 440-452, vol. 13.

Gurda et al., "Mapping a Neutralizing Epitope onto the Capsid of Adeno-Associated Virus Serotype 8," Journal of Virology, Aug. 2012, pp. 7739-7751, vol. 86, No. 15.

Li et al., "AAV-CRISPR Gene Editing Is Negated by Pre-existing Immunity to Cas9," Molecular Therapy, Jun. 2020, vol. 28, No. 6.

Mehta et al., "Immunogenicity of Cas9 Protein," Journal of Pharmaceutical Sciences, 2020, pp. 62-67, vol. 109.

Bradley et al., "Adenovirus Serotype 5 Neutralizing Antibodies Target both Hexon and Fiber following Vaccination and Natural Infection," Pathogenesis and Immunity, Jan. 1, 2012, pp. 625-629, vol. 86, Issue 1.

Fausther-Bovendo et al., "Pre-existing immunity against Ad vectors Humoral, cellular, and innate response, what's important?" Human Vaccines & Immunotherapeutics, Oct. 2014, pp. 2875-2884, vol. 10, No. 10.

Simhadri, V.L., et al., Prevalence of Pre-existing Antibodies to CRISPR-Associated Nuclease Cas9 in the USA Population, Molecular Therapy: Methods & Clinical Development, Sep. 2018, vol. 10, pp. 105-112.

Elkins, S., Identification of Patient Specific Neutralizing Epitopes on the AAV8 Virus for Personalized Gene Therapy, Masters Thesis, Harvard University, May 2020, 65 pages.

Mingozzi, F., AAV Immunogenicity: A Matter of Sensitivity, Molecular Therapy, Oct. 2018, vol. 26, No. 10, pp. 2335-2336.

Jiang, H., et al., Effects of transient immunosuppression on adenoas-sociated, virus-mediated, liver-directed gene transfer in rhesus macaques and implications for human gene therapy, Gene Therapy, Nov. 15, 2006, vol. 108, No. 10, pp. 3321-3328.

Xiao, W., et al., Impact of neutralizing antibodies against AAV is a key consideration in gene transfer to nonhuman primates, Nature Medicine, Jun. 2018, vol. 24, No. 6, pp. 699.

Verdera, H.C., et al., AAV Vector Immunogenicity in Humans: A Long Journey to Successful Gene Transfer, Molecular Therapy, Mar. 2020, vol. 28, No. 3,j pp. 723-746.

* cited by examiner a    S Q  A n t i - A A V 8  ( 5 8 1 - 5 9 6 ) A n t i b o d y  T i t e r s  a f t e r  I n d u c t i o n

A A V 8 ( 5 8 1 - 5 9 6 )  P e p t i d e  I n d u c e d  T i t e r s  ( n = 2 0 )

b    S Q  A n t i - A A V 8  A n t i b o d y  T i t e r s  a f t e r  I n d u c t i o n

A A V 8  C a p s i d  I n d u c e d  T i t e r s  ( n = 3 0 )

COMPOSITION FOR IMMUNE TOLERANCE INDUCTION AND USE IN GENE THERAPY

CROSS REFERENCE TO RELATED APPLICATION

This application claims priority to U.S. provisional patent application no. 63/139,602, filed on Jan. 20, 2021, the disclosure of which is incorporated herein by reference.

SEQUENCE LISTING

The instant application contains a Sequence Listing which has been submitted electronically in ASCII format and is hereby incorporated by reference in its entirety. Said ASCII copy, created on Jan. 12, 2022, is named "011520_01662_SEQ_ID_ST25.txt", and is 520 bytes in size.

BACKGROUND OF THE DISCLOSURE

In the treatment of monogenic diseases via introduction or modification of genes, one of the main challenges has been the successful targeted delivery of the therapeutic genes. With new discoveries in this field, it was found that viruses, which are naturally evolved to deliver their nucleic acids into host cells and undergo replication can prove to be a useful tool for the delivery of therapeutic genes. Viral vectors are the most common vectors for the delivery of transgenes. One such viral vector is Adeno-associated virus (AAV). With the identification of 13 different serotypes, this virus vector has proven to be a promising tool in gene therapy due to its high transduction efficiency, robust and sustained transgene expression in the target cells. Adenoviruses are small (~25 nm), non-enveloped DNA viruses belonging to the paroviridae family. Each serotype has distinct cellular transduction characteristics which makes them of great interest in gene therapy to be utilized as delivery vehicles. AAVs, including AAV5, AAV8, have been of prime interest in targeted gene therapy. AAVs have been exploited in gene therapy for the treatment of various diseases such as Hemophilia B, Leber's Congenital Amaurosis (LCA), Pompe disease, Diabetes Mellitus (DM) and several others under pre-clinical and clinical trial phases.

Despite all advantages of AAVs or other viral vectors, there still remain a number of barriers to successful delivery of therapeutic transgenes. One such key issue is pre-existing immunogenicity against the viral capsid. The altered gene of interest as well the viral capsid itself are the two main sources that contribute to any host immune responses encountered against the vector-mediated gene therapy. Seroepidemiological studies suggest that about 40% of common population carry neutralizing antibodies (NAbs) against AAV8 and is the least seroprevalent among all the other AAV serotypes (Vandamme et al., Hum Gene Ther. 2017; 28(11):1061-74). The presence of anti-capsid antibodies such as neutralizing class of antibodies in the circulation can block the cellular entry of viruses even at minimal titer levels. These anti-AAV8 specific pre-existing antibodies gravely affect the transduction efficiency of the viral vector and in turn prevent the transgene expression. They are also known to affect the specificity of the vectors instead digressing them to the spleen. Apart from NAbs, patients have also been known to carry capsid specific binding antibodies. Unlike NAbs, BAbs are capable of recognizing the viral capsids but do not neutralize the capsids. Binding or non-neutralizing type of antibodies are known to tag the capsids to accelerate their clearance from the system leading to a short-lived transgene expression. Due to the high homology between the different serotypes, these pre-existing antibodies are also cross-reactive. Studies have shown that subjects with pre-established antibody titers to AAV1 or AAV2, also developed a cross-reactive antibody response against AAV8 (Calcedo Front Immunol. 2013; 4:341).

Current strategies to evade pre-existing host immune responses include screening AAV variants resistant to neutralization using error-prone PCR, modification of the immunogenic domains to circumvent recognition by NAbs, capsid shuffling to produce chimeric vectors by immuno-selective selection. These approaches limit the number of viable vectors that can be produced since they may reduce the packaging capacity, and may alter the infectivity profile. Other strategies include limiting gene therapy only to naïve patients or lowering the levels of NAb titers in patients by plasmapheresis or administration of empty capsids and immunosuppression. These approaches confine the number of patients that can participate in gene therapy, fail to work in patients with high titers of NAbs and even pose problems of global immunosuppression exposing the patients to high risk of infections ((Calcedo Front Immunol. 2013; 4:341). All the above complications with the current approaches indicate a strong need for a viable strategy that can reduce AAV8 antigenicity and suppress such pre-existing humoral responses in patients with high NAb titers without affecting the viral capsid infectivity, transduction efficiency, specificity and expression profile. Similarly, pre-existing antibody against Cas9 in general population could impact the safety and efficacy of CRISPR/Cas a gene editing approach by neutralizing Cas9 activity (Simhadri et al, Mol. Ther. Methods. Clin. Dev. 2018: 10, 105-112). CRISPR/Cas holds promise not only as a biological tool but also for treating several clinical conditions. Thus, technology to reverse pre-existing antibody response against gene therapy vectors and CRISPR platform will impact positively by expanding the number of patient participating in these life-saving treatment modalities.

SUMMARY OF THE DISCLOSURE

The present disclosure provides compositions and methods for suppressing immune responsiveness to viral vector proteins. The compositions and methods are based, at least in part, on demonstration of induction of hypo-responsiveness by using lyso-PS liposomes complexed to viral vector proteins. The hypo-responsiveness of Lyso-PS is antigen-specific. As an example, this disclosure provides data to demonstrate the ability of lyso-PS liposomes to induce immune tolerance towards a 16-mer peptide, AAV8$_{581-596}$ (IVADNLQQNTAPQIG (SEQ ID NO:1)). This 16 amino acid sequence present in the viral protein III region of AAV8 vector capsid was found to be highly susceptible to being neutralized by ADK8, a monoclonal antibody employed for the determination of antigenic epitopes in the capsid (Tseng et al., Front Immunol. 2014; 5:9). Data provided in the present disclosure demonstrate that lyso-PS was able to effectively induce oral immune tolerance towards the immunogenic AAV8$_{581-596}$ peptide. Additionally, this disclosure provides data to demonstrate that the present compositions and methods can reverse pre-established capsid specific antibody titers upon oral administration. This may involve lysoPS acting on plasma and memory B-cells. The present compositions and methods can be used for gene therapy, vector vaccines and CRISPR based technologies.

In an aspect, the present disclosure provides compositions comprising lipid particles (e.g., liposomes) which comprise phosphatidylserine (PS) where some or all of the PS may be present as lysophosphatidylserine (lyso-PS) and where the liposomes are complexed to proteins or peptides from delivery vehicles (such as viral vectors used in gene therapy, gene editing, vector vaccinations and the like). The present disclosure also provides methods for inducing immune tolerance ore reducing antibody titers against delivery vehicle proteins using such compositions.

The compositions of the present disclosure comprise complexes of viral vector protein or antigenic fragments thereof and liposomes or lipid structures, wherein the liposomes or lipidic structures comprise phosphatidylserine (PS) and phosphatidylcholine (PC). At least some of the PS is present as lyso-PS. In embodiments, all of the PS may be present as lyso-PS. The liposomes may also comprise phosphatidylethanolamine (PE) in addition to PS and PC. The protein can be any protein or peptide from a viral vector, or may be a modification thereof.

The administration strategy disclosed herein can induce tolerance toward immunogenic proteins or peptides that are used in delivery of gene therapy agents. For example, pre-exposure (e.g., immunization) via oral route to particular liposomal compositions (designated here as tolerogenic or priming compositions) complexed to a target protein (such as protein or peptide from a bacterial or viral vector) can lead to hypo-responsiveness to the protein in subsequent gene delivery using those delivery vehicles. The induction of immune tolerance may be manifested as one or more of the following: down-regulated expression of co-stimulatory signals on dendritic cells, lowered $CD4^+$ T-cell proliferation and/or induced secretion of immuno-regulatory cytokines such as TGF-β and IL-10, and/or reduction in antibody titer.

The present compositions and methods are useful for induction of immune tolerance to administered viral vector protein, particularly via oral route. The present compositions and methods are also useful for reducing pre-existing antibody titers.

The process of reversal of titers against AAV and Cas9 may be mechanistically different from reversing immune response against self-proteins that are needed to treat autoimmune conditions and allergens. For example, reversal of immune response against self-proteins in type 1 diabetes would require protection using cell mediated tolerance.

In an aspect, this disclosure provides a method for reducing pre-existing antibodies against viral vector proteins. In embodiments, the pre-existing antibodies may be against adenoviral vector proteins, such as one or more of the various capsid proteins. In embodiments, the pre-existing antibodies may be against AAV8 capsid proteins.

The method of the present invention can be used for individuals who are known to have immunological intolerance to the viral vector target protein or to those whose immunological status toward a target protein is unknown. For example, the present compositions may be used for individuals who are going to be administered gene therapy or vaccine therapy using delivery vehicles comprising the target protein or peptide but have not previously exhibited an immune intolerance to the protein, or to naïve individuals (i.e., those who have not been previously administered the peptide or protein). Individuals are deemed to not have exhibited immune intolerance to a protein if there are no detectable titers of antibodies to the protein.

In embodiments, the disclosure includes inducing tolerance in an individual to one or more antigens to which antibodies in the individual may impede the function of nucleic acid editing. The nucleic acid editing includes but is not necessarily limited to therapeutic and prophylactic approaches whereby a nucleic acid editing system is introduced into the individual to facilitate the editing. Such nucleic acid systems include but are not necessarily limited to viral and CRISPR systems. As such, the disclosure includes inducing tolerance in an individual that is a candidate for nucleic acid editing (e.g., a gene therapy) to one or antigens in the pertinent editing system.

In embodiments, the disclosure provides methods of inducing tolerance for viral vector peptides used in vector vaccines. Vector vaccines are generally constructed from a carrier virus, such as an adeno or pox virus, and are engineered to carry a relevant gene from the virus (e.g., SARS-CoV-2). In this embodiment, while immune response is desired against the protein of interest from a pathogenic organism inserted within the genetic material of the delivery virus vehicle, a dampening of immune response is desired against the viral vector protein itself. As such, the present compositions and methods can be used for selective suppression of pre-existing or de novo immune response against delivery vehicle components of vaccine compositions.

In embodiments, tolerance is induced to any antigen that is comprised by any of the following viral-based delivery nucleic acid editing systems: Adenovirus, such as recombinant adeno-associated viruses (rAAVs), Retroviruses, Lentiviruses, Herpes Simplex Virus (HSV), and Baculovirus.

In a non-limiting embodiment, tolerance is induced in an individual who has pre-existing anti-adenovirus (Ad) neutralizing antibodies (AdNAbs). In embodiments, such antibodies bind to an antigen associated with any type of Adenovirus, including but not limited to adeno-associated virus serotype 2, adenovirus serotype 5, and adenovirus serotype 8. In embodiments, such antibodies bind to an Adenovirus capsid protein. In embodiments, the antibodies bind to adenovirus fiber and/or penton base proteins.

In embodiments, tolerance is induced to any CRISPR associated agent that is intended to function in a human or non-human individual that can produce antibodies. In embodiments, tolerance is induced to any CRISPR associated antigen that is comprised by any CRISPR associated enzyme (e.g., a Cas enzyme), including any member of any Type or Class of Cas enzymes. In embodiments, the Cas is a Type I, Type II, or Type III Cas enzyme. In non-limiting embodiments, the Cas is Cas9 or Cas12a (also referred to as Cpf1).

DETAILED DESCRIPTION OF THE DISCLOSURE

Figure 1:
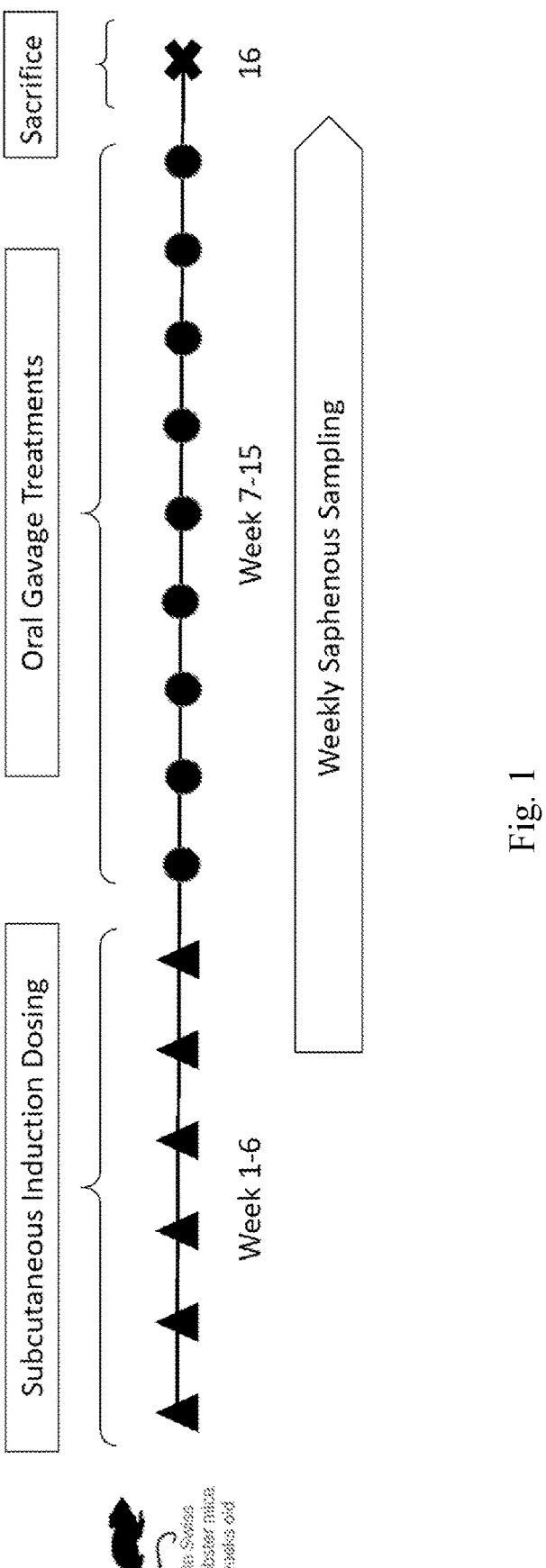
FIG. 1: In-vivo Reversal Study Design. Mice are given subcutaneous injections for 4-6 consecutive weeks (week 1-6) for induction of antibody titers specific to antigens (for e.g., AAV8 capsid, $AAV8_{581-596}$ peptide, AAV5, Cas9). After the induction of antibody titers, these mice were segregated into their respective treatments groups and given weekly oral gavages starting at week 5-7 through week 17. This was followed by a washout period of 1-2 weeks. Blood is collected from animals every week starting at week 1 through the entire duration of study via saphenous vein puncture for monitoring the antibody titer levels.

The term "target protein" as used herein means any protein to which an immunological hypo responsiveness is desired. For example, a target protein may be a protein or peptide from a microbe or a modification thereof that is used as a delivery vehicle (e.g. for delivery of polynucleotides).

By "specific" immunological response is meant that an immune response to non-relevant proteins (proteins that were not complexed to the liposomes of the priming composition) is not affected.

By "administered" or "administration" is meant that the protein or peptide is delivered to the individual or introduced into the individual's body by any means or route of delivery.

By "inhibitory" titers or antibodies in reference to a protein or antigen is meant specific antibodies generated against the protein or antigen.

By "lipidic structures" is meant liposomes and other structures such as micellar structures, liposomes, cochleates, molecular assemblies and the like.

The term "lyso" when used herein in conjunction with a phospholipid means that the glycerol part of the molecule has only one acyl chain instead of two. For example, lyso-PS has only one acyl chain as compared to PS which has two acyl chains.

By reference to protein complexed to liposomes or liposomes complexed to protein, it is meant that the protein may be associated with the particle in one or more of the following configurations including location in the lumen of the particle, partly or fully intercalated in the bilayer or bound or adsorbed to the surface of the particle. As an example, data is provided herein for liposomes-protein complexes for adeno-associated virus (AAV) capsid protein.

Liposomes may be referred to herein as lipidic nanoparticles, or nanoparticles. The phospholipids for preparing the liposomes can be obtained from any available source, such as, for example, from a plant or an animal. The phospholipids are commercially available or can be synthesized by known methods. For example, phosphatidylserine (PS) can be obtained from porcine brain PS or plant-based soy (e.g., soya bean) PS. Lyso-PS is also available commercially. For purposes of this description, while examples of protein complexes or induction of immune tolerance may refer to specific proteins, it is equally applicable to other proteins.

Abbreviations: Adeno-Associated Virus, AAV; Viral Protein, VP; Inverted Terminal Repeats, ITR; Recombinant Adeno-Associated Virus, rAAV; Neutralizing Antibodies, NAbs; wtAAV, wild-type AAV; Binding Antibodies, BAbs; Immunoglobulin G, IgG; Dendritic Cells, DCs; Interleukin 10, IL-10; Transforming Growth Factor beta, TGF-β; Regulatory T-cells, Tre g s; T-cell independent antigens, TI; T-cell dependent antigens, TD; Microfold cells, M-cells; Gut-Associated Lymphoid Tissue, GALT.

The present disclosure provides compositions and methods for suppression of immune response toward viral vector proteins in therapeutic or prophylactic treatment of conditions using viral vector delivery vehicles. The method of the disclosure comprises administering to an individual in whom a suppression of the immune response is desired, a composition comprising liposomes or other lipid structures comprising phosphatidylcholine (PC) and PS, wherein some or all of the PS is present as lyso-PS and wherein the liposomes or lipid structures are complexed with proteins or peptides of the viral vector, or fragments or modifications of such proteins or peptides. For example, any of the proteins or fragments thereof, or peptides encoded by Adenoviral vectors (or any other viral vectors) may be used, such as AAV serotypes from AAV1-AAV11, All subtypes of Ad A through G. The sequences of these and other proteins are well known. The UniProt accession numbers are A0A0S0C249, A0A0S0DU13, A0A0S0DSV8 (VP1 fragment), Q6JC62 (Capsid protein VP1), Q8JQF8 (Capsid protein), B4Y886 (Capsid protein VP1 fragment), Q9YIJ1 (AAV5), Q8JQF8 (AAV8), Q99ZW2 (spCas9), P04133 (ad5 hexon). Additional accession numbers are saCas9: J7RUA5, stCas9:G3ECR1, cas12a: U2UMQ6, cas13a: PODOC6, PODPB7, C7NBY4, U2PSH1.

In embodiments, the viral vector protein that is complexed to lyso-PS liposomes may be any capsid protein or a fragment thereof. Generally, the fragments may be from 6 to 32 amino acids and all integer values and ranges therebetween. For example, the capsid proteins or fragments thereof maybe from AAV2, AAV5, or AAV8. In embodiments, the viral vector protein is $AAV8_{581-596}$. The resulting liposome complexed with a viral vector protein may be referred to as a liposome complex.

The present disclosure can be used to reduce pre-existing antibodies against viral vectors used in DNA vaccine formulations. For example, AD5, AD26 and variants thereof (e.g., variant of AD26 that is derived from chimp AD) may be used.

In embodiments, the viral vector may be any viral vector that is used for delivery of nucleic acids to a mammalian host. Examples include, but are not limited to adenovirus, such as recombinant adeno-associated viruses (rAAVs) (which may be interchangeably referred to herein as adenoviral vectors), Retroviruses, Lentiviruses, Herpes Simplex Virus (HSV), and Baculovirus. Examples of proteins from the viral vectors include capsid proteins and antigenic fragments thereof. The method may comprise administering to an individual in need of treatment a composition comprising the viral vector protein or peptide or an antigenic fragment thereof complexed to liposomes comprising PC and lyso-PS.

The present liposomes can be prepared by trigger loading technique as described herein and illustrated in the examples. As a first step, conformationally altered state of the protein or peptide is generated by increasing the temperature and/or decrease in pH. For example, $AAV8_{581-596}$ can be loaded on to the liposomes by exposing to an elevated temperature which will result in unfolding of the peptide (such as up to 70° C.). In embodiments, it may be heated up to from room temperature to 70° C., such as from 30° C. to 65° C. Alternatively, or in addition, the pH may be lowered, such as from 3 to 8 to induce conformational changes. When incubated with the lyso-PS liposomes in this state, the peptide is able to intercalate into the liposomal bilayer. The liposomes can then be cooled down to room temperature (generally between 18 to 25° C., such as, 18, 19, 20, 21, 22, 23, 24, or 25° C.). The pH range can be from 3 to 8 (e.g., 3, 4, 5, 6, 7, or 8). The present liposome compositions can be stored at room temperature in the freeze dried state for several months or in liquid or reconstituted state for up to 48 hours (hrs), in the freezer for months, and refrigerated conditions in solid state for months and in liquid state for weeks.

In embodiments, the association may be at least 40%, 50%, at least 60%, at least 70%, at least 80%, or at least 90%. In embodiments, the association may be from 80 to 99%, 75 to 99%, 75 to 95%, or 80 to 95%. In embodiments, the association may be from 80, 81, 82, 84, 85, 86, 87, 88, 89, 90, 91, 92, 93, 94, 95, 96, 97, 98, 99, or 100%.

The liposomes and other lipid structures comprise PC and PS, some or all of which may be in the form of lyso-PS. The liposomes or other lipid structures may contain PS (or lyso-PS) and PC as the only phospholipids. The PS or lyso-PS may be in a range of from 10% to 50% of the total phospholipids in the bilayer and the percent is mol %). 1 to 100% (and all values and ranges therebetween) of the PS may be in the form of lyso-PS. For example, the liposomes may have PC:lyso-PS as 90:10, 80:20, 70:30, 60:40, or 50:50 molar ratios. In an example, the lyso-PS can be from 15 to 50 molar %, the remaining phospholipids being PC. For example, the lyso-PS can be from 15 to 30%. Whenever a range is mentioned in this disclosure, all values within that range are also included. In one example, only the PS (some or all) is in the form of lyso-PS, while all of the PC has two acyl chains. All ratios of phospholipids in this disclosure are molar ratios, unless otherwise stated.

In one example, the lipidic structures, such as liposomes, in which from 30 to 100% of the PS is present as lyso-PS, further comprise retinoid acid and/or rapamycin. Thus, the lipidic structures can comprise PS (some or all of which can be lyso-PS), PC and retinoid acid and/or rapamycin. The amount of retinoic acid can be from 0.1 mol % to 10 mol % and all percentage values to the tenth decimal place therebetween. The amount of rapamycin can be 0.1 mol % to 10 mol % and all percentage values to the tenth decimal place therebetween.

The acyl chains can be saturated or unsaturated. The acyl chains of the PC may be 12 to 22 carbons in length. The acyl chains are preferably both of the same length and saturated. It was observed that a chain length of 14 (C14:0, dimyristoyl-sn-glycero-3 phosphatidylcholine (DMPC)) was particularly effective in providing stability to the liposomes. When a chain length of 18 (1,2-Distearoyl-sn-glycero-3-phosphocholine (DSPC)) was used, it was found to be not as effective as DMPC.

The lyso-PS acyl chain may be unsaturated. It can be 14 to 22 carbons in length. It should have at least one double bond. For example, it can be 18:1 (where 18 represents the number of carbon atoms and 1 represents the number double bonds). In various examples, the acyl chain may have 2 or 3 double bonds, although the stability of the liposomes was found to be the better with a single double bond than with 2 or 3 double bonds. However, at least one double bond was found to be necessary for enhanced tolerance.

At least some of the PS is lyso-PS, but the PC is not lyso-PC. Thus, all of the PC has two acyl chains and at least some PS has only one acyl chain. For example, the PC:PS ratio is 90:10 to 60:40, where all of the PS is lyso-PS. For example, the PC:lyso-PS may be 85:15 to 65:35. In an example, the ratio of PC:lyso-PS may be 70:30. In an example, the lyso-PS is from 15 to 50% or 15 to 35% where the remaining phospholipids are PC. The lyso-PS and PC may be the only phospholipids present in the bilayer of the liposomes. The total lyso-phospholipid in the liposomes is preferably less than 50% of the total phospholipid because if the lyso-phospholipid percentage is higher than 50%, the liposomes are not stable.

The present liposomes may further comprise additional phospholipids. For example, any of the liposomes described herein may comprise phosphatidylethanolamine (PE). The amount of PS, some or all of which may be lyso-PS, may be 0 to 30 mol %, the amount of PC may be 0 to 30 mol %, and the remaining may be PE. For example, PS, some or all of which may be lyso-PS, may be from 1 to 30 mol %, PC may be from 1 to 30 mol % and the remaining can be PE.

The liposomes comprising lyso-PS as described herein were found to be smaller than the liposomes comprising only PS (without any lyso-PS). For example, after filtration through a 0.2 micron cutoff filter, the size of the lyso-PS containing liposomes (liposomes comprising lyso-PS and PC) was about 50-150 nm (about 90% of the liposomes), while the size of PS containing liposomes (PS+PC) was about 200-400 nm (about 90% of the population). It was surprising that the even though the lyso-PS liposomes are smaller than the PS liposomes, the charge is not as negative. The zeta potential for the lyso-PS liposomes is −10 to −17 compared to a zeta potential of −24 to −33 for PS liposomes, and −17 to −26 for size-matched PS liposomes. The less negative charge on the lyso-PS liposomes may enable increased loading of proteins. For example, for PS liposomes, a typical protein:lipid ratio is 1:10,000 molar ratio, but for lyso-PS liposomes, the protein could be loaded and used at least up to 1:5,000 molar ratio. Proteins can be loaded on to the lyso-liposomes at molar ratios from 1:1,000 to 1:10,000 (and all ratios therebetween) or 1:100 to 1:10, 000 (and all ratios therebetween).

In an aspect, the present disclosure provides compositions comprising liposomes. For example, the composition may comprise a plurality of liposomes described herein in a suitable carrier. A suitable carrier may be a buffer or other pharmaceutical carriers or additives, excipients, stabilizers, or a combination thereof. For example, the liposomes may be formulated in sugars, starches, cetyl alcohol, cellulose, powdered tragacanth, malt, gelatin, talc, oils, glycols, glycerol monooleate, polyols, polyethylene glycol, ethyl alcohol, additional emulsifiers and the like. Examples of pharmaceutically acceptable carriers, excipients, and stabilizers can be found in *Remington: The Science and Practice of Pharmacy* (2012) 22nd Edition, Philadelphia, PA. Lippincott Williams & Wilkins.

The present priming composition can be formulated for oral delivery. The composition may be directly delivered to the desired location in the gastrointestinal tract using gavage. Or they can be formulated in the form of liquid, suspensions, tablets (including enteric coated tablets), gels, capsules, powder or any other form that can be ingested. Formulations can include pharmaceutical carriers known to be used for oral formulations. The formulations can be pediatric formulations, which can include various flavors and the like.

The present compositions are useful for not only inducing immune tolerance, but are also useful for reducing antibody titers of existing antibodies, which was surprising.

In some embodiments, the present method comprises administering to an individual a first composition (also referred to herein as a priming composition), which can comprise one or more administrations or doses comprising a target protein (such as a viral vector protein) complexed with liposomes comprising PS and PC (referred to herein as PS liposomes), where at least some of the PS may be present as lyso-PS. In embodiments, all of the PS may be present as lyso-PS. The administration(s) of the priming composition(s) can be followed up with gene therapy, CRISPR-mediated gene editing or vector vaccinations, where the gene therapy, CRISPR-mediated gene editing or vector vaccinations comprise administering a viral vector that comprises the gene encoding the viral protein as well as the therapeutic or immunizing protein gene. The priming compositions can be administered once weekly or more times a week. For example, the priming composition can be administered once a week or two to six times a week or may be administered daily. Administration can be carried out for 1, 2, 3, 4, 5, 6 or more weeks, and then stopped. The therapeutic or immunizing compositions can be delivered any time prior to, overlapping with, or after the cessation of the priming composition administration regimen. In an embodiment, after a suitable period of time allowing immune tolerance to develop (such as, for example, at least 4 days after the last primer), the individual can be administered gene therapy/vector vaccine composition.

In embodiments, the priming compositions only contain proteins or antigenic fragments thereof from the viral vectors and do not contain the therapeutic or immunizing proteins.

In an embodiment, the priming composition may be administered for up to several weeks. As an example, the priming composition may be administered for 4 weeks. The frequency of oral administration of the priming composition (such as protein-lyso PS liposomes) can be once-a-week or more for four weeks. More doses of protein-lyso PS can also be used.

The priming composition may be administered one time or multiple times, and may be administered on an ongoing basis (continuous administration). Similarly, the second (therapeutic composition or vaccinating composition) composition may be administered one time or multiple times, or an ongoing basis (continuous administration), or administered intermittently as needed. The second composition can administered together with or after allowing a head-start with the first composition, such as after 1 to 6 weeks of the start of the first composition, or may be administered or started at the same time or within 1 to 6 weeks of the start of the first composition. In an embodiment, the priming composition may be administered on a continuous schedule and the second composition (also referred to herein as a therapeutic composition) may be administered after a time lag after the start of administration of the priming composition, but overlapping the administration schedule of the first composition. Thus, the administration of the second composition may occur concurrently with the administration of the first one, after a period of initial administration of the first composition only.

In embodiments, one or more doses of a priming composition can be administered on an on-going basis over a period of time to reduce existing antibodies or reduce generation of antibodies against vector delivery vehicle proteins. Thus, the regimen of administration can involve administration on a substantially regular basis, which administration may be, for example, daily or weekly, or may be more or less frequent, and may be administered via any route. Such as administration regimen may be carried out for weeks, months, or years. The intervals between the consecutive administrations may be same or different, but will generally maintain the periodicity of administration.

This composition can be used for any individual (e.g., a human or a non-human mammal). The individual may or may not be showing indications of a recent immune intolerance. It is also useful for administration to naïve individuals (i.e., those individuals who have not been administered the protein or peptide previously). Immune intolerance as used herein means the individual should have measurable (by standard methods such as ELISA or activity assays) antibody production. Conversely, a lack of immune intolerance (or a state of immune tolerance) means the individual has no measureable antibodies. The antibodies may be measured after exposure to or administration of free form of the protein after an individual has been "tolerized". The term tolerized as used herein means administration of one or more doses of priming composition and a suitable length of time (such as from 4 to 30 days) for an individual to develop immune tolerance. Development of immune tolerance against the target protein can also be identified by determining down-regulated expression of co-stimulatory signals on dendritic cells, lowered CD4$^+$ T-cell proliferation, and induced secretion of immuno-regulatory cytokines TGF-$\beta$ and IL-10. One or more of these identifiers can be evaluated in culture conditions. The development of immune tolerance is specific to the protein against which tolerance is induced (i.e., the protein complexed with the liposomes of the priming composition).

In an embodiment, the priming composition may be administered and then a determination of induction of immune tolerance may be made by evaluating one or more of the following: down-regulated expression of co-stimulatory signals on dendritic cells, lowered CD4$^+$ T-cell proliferation, induced secretion of immuno-regulatory cytokines TGF-$\beta$ and IL-10, or lowered antibody titer compared to prior to administration of the priming composition. Upon confirmation of induction of immune tolerance to the viral vector proteins, administration of gene therapy or vaccination can be carried out.

The following Statements provide various embodiments of the present disclosure:

Statement 1. A method of reducing existing antibody titers directed to a viral vector protein comprising administering to an individual in need of treatment a composition comprising liposomes, wherein the liposomes comprise phosphatidylcholine (PC) and lysophosphatidylserine (lyso-PS), wherein the ratio of PC to lyso-PS is from 90:10 to 60:40, wherein some or all of the PS is present as lyso-PS and wherein the liposomes are complexed to the protein or an antigenic fragment thereof.

Statement 2. A method according to Statement 1, wherein the acyl chain of the lyso-PS is oleic acid.

Statement 3. A method according to Statement 1 or Statement 2, wherein all of the PS is present as lyso-PS.

Statement 4. A method according to any one of the preceding Statements, wherein the ratio of PC to lyso-PS is from 85:15 to 70:30.

Statement 5. A method of claim 1, wherein the PC is present as dimyristoyl-sn-glycero-3 phosphatidylcholine (DMPC).

Statement 6. A method of claim 1, wherein the peptide is a capsid protein or Cas protein.

Statement 7. A method of claim 1, wherein the sequence of the peptide is IVADNLQQNTAPQIG (SEQ ID NO:1).

Statement 8. A method of reducing generation of antibodies against a viral vector protein comprising administering to an individual in need of treatment a composition comprising liposomes, wherein the liposomes comprise phosphatidylcholine (PC) and lysophosphatidylserine (lyso-PS), wherein the ratio of PC to lyso-PS is from 90:10 to 60:40, wherein some or all of the PS is present as lyso-PS and wherein the liposomes are complexed to the protein or an antigenic fragment thereof.

Statement 9. A composition comprising liposomes, wherein the liposomes comprise phosphatidylcholine (PC) and lysophosphatidylserine (lyso-PS), wherein the ratio of PC to lyso-PS is from 90:10 to 60:40, and wherein the liposomes are complexed to a protein or an antigenic fragment thereof encoded by a viral vector.

Statement 10. A composition according to Statement 9, wherein the acyl chain of the lyso-PS is oleic acid.

Statement 11. A composition according to Statement 9 or Statement 10, wherein the ratio of PC to lyso-PS is from 85:15 to 70:30.

Statement 12. A composition according to any one of Statements 9-11, wherein the PC is present as dimyristoyl-sn-glycero-3 phosphatidylcholine (DMPC).

Statement 13. A composition according to any one of Statements 9-12, wherein the protein or peptide is viral capsid protein or peptide.

Statement 14. A composition according to any one of Statements 9-13, wherein the protein is a Cas protein.

Statement 15. A composition according to any one of Statements 9-13, wherein the sequence of the protein or peptide is IVADNLQQNTAPQIG (SEQ ID NO:1).

Statement 16. A composition according to any one of Statements 9-13, wherein the protein or peptide is Ad5.

Statement 17. A composition according to any one of Statements 9-14, wherein the Cas protein is Cas9.

The following examples are provided for illustrative purposes and are not intended to be limiting.

Example 1

The following provides description of synthesis and use of liposomes and liposome complexes of the present disclosure.

Materials and Methods

Lysophosphatidylserine (Lyso-PS) and dimyristoylphosphatidylcholine (DMPC) were purchased from Avanti Polar Lipids (Alabaster, AL) and stored at −80° C. in chloroform. AAV8, AAV5 capsid were obtained from Vigene Biosciences (Rockville, MD). AAV8$_{581-596}$ peptide was purchased from GenScript and reconstituted in sterile water (Piscataway Township, NJ). Tween 20, hydrogen peroxide, and phosphorus solution standards were obtained from Sigma (Saint Louis, MO). Fetal bovine serum was purchased from Biowest (Riverside, MN). Rhodamine PE was purchased from Avanti Polar Lipids (Alabaster, AL). Alkaline phosphatase-conjugated goat anti-mouse Ig antibody was purchased from Southern Biotech (Birmingham, AL). Horseradish peroxidase-conjugated goat anti-mouse IgG antibody and 3,3',5,5'-tetramethylbenzidine substrate (TMB) were purchased from Sigma Aldrich (St. Louis, Missouri). Endosafe Endochrome-K® Kit was purchased from Charles River Laboratories (Charleston, SC). NUNC MaxiSorp 96 well plates were purchased from Thermo Fisher Scientific (Rochester, NY). CD21/CD35 monoclonal antibody (8D9), PE conjugate [12-0211-82] and CD23 monoclonal antibody (B3B4), FITC conjugate [11-0232-81] were obtained from eBiosciences™. Swiss-webster mice were obtained from Charles River Laboratories (Charleston, SC).

Animals

Eight week old male Swiss-Webster mice were purchased from Charles River Laboratory (Kingston, NY), and maintained on site. All animal experiments were approved by and followed as per the guidelines approved by the Institutional Animal Care and Use Committee (IACUC) guidelines implemented by University at Buffalo, the State University of New York. At the end of the experiment, mice were sacrificed via cardiac puncture while under isoflurane anesthesia.

Preparation of Lyso-PS Nanoparticles

Lyso-PS liposomes were prepared at a molar ratio of 30:70 Lyso-PS to DMPC. A rotary evaporator (Buchi-R200, Fisher Scientific) was used for the formation of a lipid film by evaporation of the chloroform solvent. The lipid film was then rehydrated in Tris-Calcium Chloride buffer (1×, pH 7.4) and incubated at 37° C. Extrusion of liposomes was carried out several times through double stacked polycarbonate membranes with 200 nm pore size using a nitrogen pressure extruder (Mico, Inc., North Mankato, WI). The liposomes were then sterilized by filtration using a 0.2-μm pore size syringe filter (Corning, NY). Tris-Calcium chloride buffer was tested for endotoxin and was confirmed to be endotoxin negative. The protein to lipid molar ratio was 1:10,000 for treatment groups receiving AAV8 capsid and protein to lipid molar ratio was 1:1,000 for treatment groups receiving AAV8$_{581-596}$ peptide. The association of AAV8 capsid to lyso-PS liposomes and AAV8$_{581-596}$ peptide to lyso-PS liposomes was achieved by incubating the two complexes at 37° C. for 30 minutes, which allowed for the protein and peptide to be trigger-loaded into the liposomes. Phosphate assay was performed to confirm the lipid content of the final liposome formulation and the size distribution of liposomes was determined using a NICOMP Model CW380 particle size analyzer from Particle Sizing Systems (Port Richey, FL).

Determination of Association Efficiency of AAV8$_{581-596}$ Peptide to Lyso-PS Liposomes Association efficiency of the amount of protein associated with PS liposomes was assessed previously using Size-exclusion Column Chromatography. The size exclusion column prepared using G-50 sephadex beads. The liposomes were fluorescently labelled with rhodamine-PE so as to detect them as they elute off the column. The lipid mixture was incorporated with one mole percent of rhodamine phosphatidylethanolamine (PE) before evaporation and liposomes were subsequently prepared as described in the previous segment. LysoPS-rhodamine liposomes were complexed with AAV8$_{581-596}$ using 500 μg/ml of AAV8$_{581-596}$ in a 1:50 protein to lipid ratio. Fractions of eluents were collected from the column after the run. The content of liposomes was determined by measuring fluorescence of rhodamine, by excitation at 560 nm and emission at 583 nm. The protein content in each fraction was quantified by a Micro-BCA assay kit (ThermoFisher, Waltham, MA).

Determination of Association Efficiency of AAV8 Capsid to Lyso-PS Liposomes

Association efficiency of the amount of protein associated with PS liposomes was assessed previously using a Nanosep 30K Centrifugal device (Pall Laboratories, Port Washington, NY). Liposomes were prepared as described in the previous segment. The LysoPS-AAV8 complex was made using 30 μg/ml of AAV8 in a 1:10,000 protein to lipid molar ratio. This complex was incubated at 37° C. for 30 minutes. The sample of the LysoPS-AAV8 complex was loaded into the Nanosep device and centrifuged at 9,300×g for 5 min at 25°

C. The pellet obtained after the centrifugation run was collected and assayed using a Micro BCA protein assay kit (ThermoFisher, Waltham, MA). The encapsulation efficiency was reported to be the mean after the three runs of this experiment.

Induction of Anti-AAV8 Antibody Titers in Swiss Webster Mice

Figure 2:
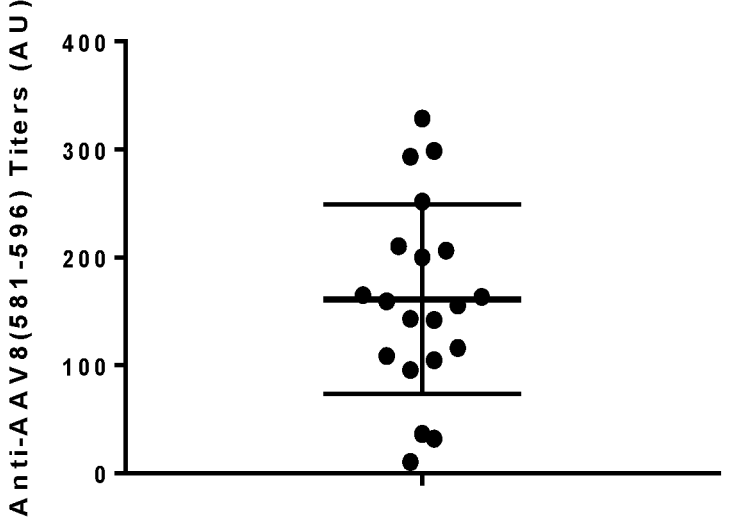
FIG. 2: Subcutaneous Anti-AAV8 Antibody Titer Induction. The anti-AAV8 antibody titers of the 20 animals from group 1 that were administered 1 µg of free $AAV8_{581-596}$ peptide are shown in panel a. and the antibody titers of 30 animals that were administered 1 µg of free AAV8 capsid protein are depicted in panel b.
Figure 2:
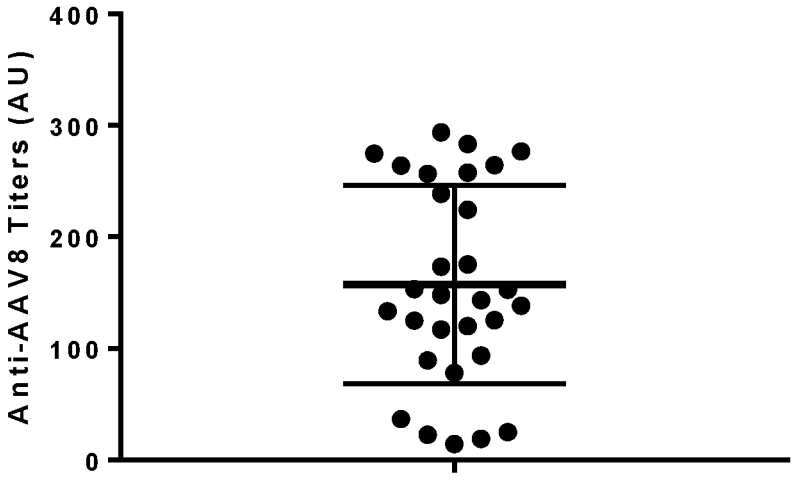

Fifty naïve, untreated 8 weeks old Swiss Webster male mice were first divided into 2 different groups with Group-1 containing 20 mice and Group-2 containing 30 mice in it. For the induction of anti-AAV8 antibody titers specific to the AAV8 peptide and AAV8 capsid, the two groups received weekly subcutaneous injections. Group-1, received a 1 µg subcutaneous dose of free $AAV8_{581-596}$ peptide for 6 consecutive weeks. Group-2, received a 1 µg subcutaneous dose of free AAV8 capsid for 6 consecutive weeks (FIG. 1). All subcutaneous injections were given to animals under anesthesia and fluid replenishment was done at the end of every injection as per the IACUC protocol. Blood was collected via saphenous vein a week after each subcutaneous injection. The blood samples were spun at 5000 g for 5 minutes and plasma was collected and stored at −80° C. The total anti-AAV8 antibody titer levels were measured from week 1 through week 6 of subcutaneous injections. Administration of free antigens (AAV8 capsid and $AAV8_{581-596}$ peptide) was stopped after animals in groups-1 and -2 reached comparable antibody titer levels. Animals that did not produce comparable titers were excluded from the study and rest of the animals were used to carry out the reversal study. 16 mice from Group-1 and 24 mice from Group-2 were chosen for the reversal study following antibody titer induction and the rest were sacrificed. FIG. 2 illustrates the grouping of animals used.

Reversal of Pre-Induced Anti-AAV8 Titers in Swiss Webster Mice

A total of 40 animals with pre-existing anti-AAV8 antibody titers were used for this study. Animals from Group-1 (FIG. 2) were divided into 2 treatment groups: "Lyso-peptide" and "Lyso-capsid 1". Mice from Group-2 (FIG. 2) were divided into 3 different treatment groups with each group containing 8 animals. The treatment groups were as follows: "Lyso-capsid 2", "Free capsid", "Buffer". The animals from lyso-peptide group were fed 1 µg dose of lyso PS-$AAV8_{581-596}$ peptide formulation in a protein to lipid molar ratio of 1:1,000. Mice from lyso-capsid 1 group carrying pre-established antibody titers to $AAV8_{581-596}$ peptide were fed 1 µg dose, which is roughly $2 \times 10^6$ gc/kg of AAV8 capsid complexed with lyso-PS liposomes in a protein to lipid molar ratio of 1:10,000. Animals from lyso-capsid 2 group having pre-induced antibody titers to full AAV8 capsid were fed the same formulation as lyso-capsid 1 group, consisting of 1 µg (~$2 \times 10^6$ gc/kg) of AAV8 capsid complexed with lyso-PS liposomes in a protein to lipid molar ratio of 1:10,000. The positive control group was administered 1 µg ($2 \times 10^6$ gc/kg) of free AAV8 capsid and the negative control group was administered tris calcium chloride buffer alone. All animals were given their respective formulations via an oral gavage for 9 consecutive weeks. For each weekly dose, the volume of oral injection given was 100 µL. Blood samples were taken prior to each week's dose and were collected weekly at weeks 7, 9 11, 13, and 15 to analyze for anti-AAV8 capsid and peptide specific antibody titers. Terminal blood samples were collected via cardiac puncture for titer analysis and spleen was collected to be analyzed by flow cytometry.

Determination of Anti-AAV8 Antibody Titers

Antibody titers were determined by ELISA using Frey method of titer analysis. According to this method, the endpoint titer is defined by the reciprocal of the highest analyte dilution that reads an absorbance value above the cut-off value. For the determination of cut-off value or "upper prediction limit", a mathematical formula was employed, according to which upper prediction limit is expressed as the standard deviation multiplied by a factor based on the number of negative controls and the confidence level ($1-\alpha$). Unlike other methods that establish the cut-off value arbitrarily, this method allows for the calculation of upper prediction limit using the Student t-distribution. For this immunoassay, 96-well Maxisorb plates were used. The determination of anti-$AAV8_{581-596}$ antibody titers was performed by coating the plates with 50 µL of 5 µg/mL $AAV8_{581-596}$ peptide in sodium carbonate-bicarbonate buffer and allowed to incubate for overnight at 4° C. For the determination of anti-AAV8 capsid antibody titers, the plates were coated with $8 \times 10^7$ AAV8 capsid vector genomes in a 100 µL volume. The plates were then washed six times with phosphate buffer containing 0.05% w/v Tween 20. Non-specific binding was blocked using 200 µL of a 0.1% w/v solution of 1% Casein in phosphate buffer and was incubated for two hours at room temperature. The plasma samples were subjected to a three-fold dilution. The plates were washed after incubation and 50 µL of each sample were added to the plate in duplicate. Three control samples were used from naïve, untreated animal and blocking buffer was added in triplicate along with sample run to account for inter-plate variability. Controls were added to the plate in triplicate. The samples were incubated for two hours at 37° C., and are washed again. 100 µL of a 1:5,000 dilution of goat anti-mouse immunoglobulin-peroxidase in blocking buffer was added to each well, and was incubated for two hours at 37° C. Plates were washed again and 100 µL of 3,3',5,5'-tetramethylbenzidine was added to each well and incubated for 45 minutes at room temperature without exposing it to light. After 45 minutes, the reaction is stopped by the addition of 100 µL of 1N hydrochloric acid to each well, and the color intensity is read at 450 nm using a Spectramax plate reader. Total antibody titers were determined using plasma samples obtained from weekly blood collections and were analyzed to be compared among the different treatment groups.

Statistical Analysis

All statistical analyses were performed using GraphPad Prism 8 (La Jolla, CA). One-way ANOVA followed by Tukey's post-hoc analysis was performed as indicated. Non-parametric Kruskal-Wallis test with Dunn's post-hoc analyses were performed. P values <0.05 were considered statistically significant and significance is denoted by * where applicable.

Association Efficiency of $AAV8_{581-596}$ Peptide and AAV8 Capsid to Lyso-PS Nanoparticles The association efficiency of $AAV8_{581-596}$ peptide to lyso-PS nanoparticles was determined by size-exclusion chromatography in tris-calcium chloride buffer (pH 7.4) at 37° C. Lyso-PS nanoparticles, around 200 nm in diameter were eluted through a sephadex column with G-50 beads to separate free peptide from $AAV8_{581-596}$ peptide associated to the nanoparticles. In tris-calcium chloride buffer at 37° C., the mean association efficiency was found to be 38.3% with a standard deviation of 9%. Association efficiency was reproducibly achieved along with acceptable protein recovery of 19.1 µg. The association efficiency of the capsid protein to nanoparticles was confirmed using nanosep 30K centrifugal device and the protein content was analyzed using a micro-BCA assay. The mean encapsulation efficiency of AAV8 capsid to lyso-PS nanoparticles from 3 independent runs was found to be 40.7% with a standard deviation of 8.8%. These results show that a viable lyso-PS associated AAV8 capsid as well AAV8$_{581-596}$ peptide nanoparticle was achieved. The complete data is shown in Table 1, which shows the association efficiency of AAV8$_{581-596}$ peptide and AAV8 capsid to lyso-PS nanoparticles. Results from 3 different size exclusion chromatography experiments using Sephadex G-50 beads are shown. The encapsulation efficiency of AAV8 capsid to lyso-PS nanoparticles was determined using a nanosep 30K centrifugal device and micro-BCA assay was used for the quantification of free and encapsulated protein. Results from 3 independent runs are as stated in Table 1. The mean±SD association efficiency was reported in the results.

TABLE 1

| | Association efficiency (%) of LysoPS-AAV8$_{581-596}$ Complex | Association efficiency (%) of LysoPS-AAV8 Capsid Complex |
| --- | --- | --- |
| Run 1 | 29.8 | 50.5 |
| Run 2 | 47.8 | 36.8 |
| Run 3 | 37.2 | 38.1 |
| Mean | 38.3 | 40.7 |
| SEM | 4.52 | 4.32 |

Orally Administered Lyso-PS-AAV8$_{581-596}$ Complex Induces Tolerance Towards AAV8 581-596

Swiss Webster mice were fed lyso-PS-AAV8$_{581-596}$ peptide complex for 9 weeks. At week 6, the animals were challenged with free peptide given via subcutaneous administration. If Lyso-PS induce tolerance, then the mice that are pre-exposed to LysoPS-AAV8 peptide will show hypo-responsiveness upon re-challenge compared to animals that are pre-exposed to free antigen or sham-treated animal. Saphenous blood samples were collected during week 9 and week 10. Anti-AAV8$_{581-596}$ antibody titer levels were measured. On week 10, Lyso-PS-AAV8$_{581-596}$ displayed significantly (p value=0.0162) lower anti-AAV8$_{581-596}$ titer levels when compared to the control buffer treated group. The LysoPS-AAV8$_{581-596}$ group had a mean SEM of 75.713.3, the free AAV8$_{581-596}$ was 164.922.5, and the buffer treated group was 187.737.4. These data suggest that Lyso-PS induced tolerance.

Figure 3:
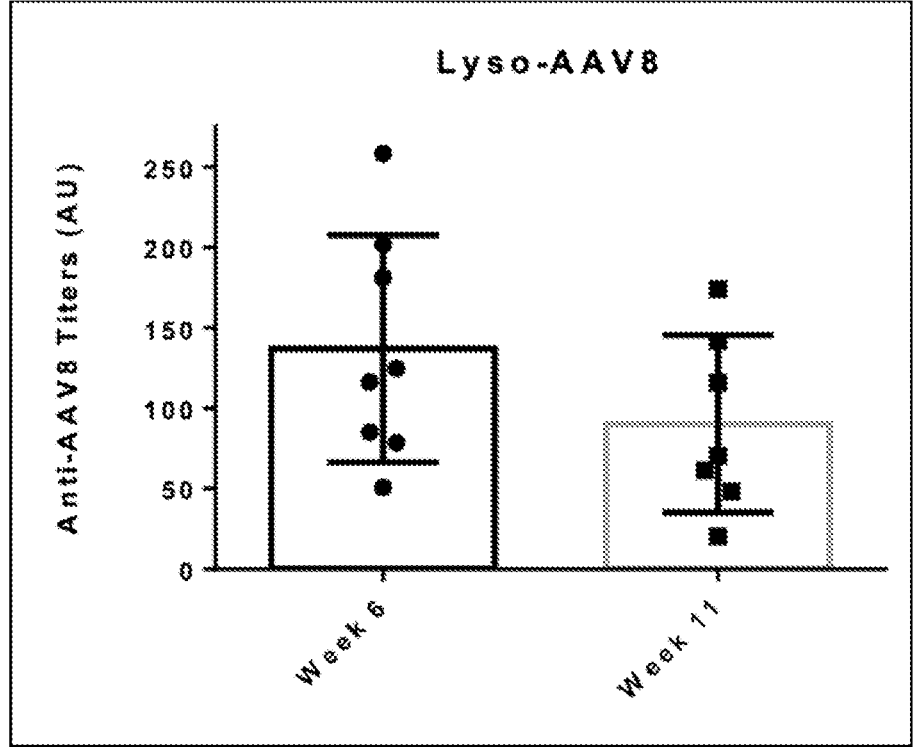
FIG. 3: Anti-AAV8 capsid/viral particle Antibody Reversal Titer Levels after Oral Gavage.
Figure 4:
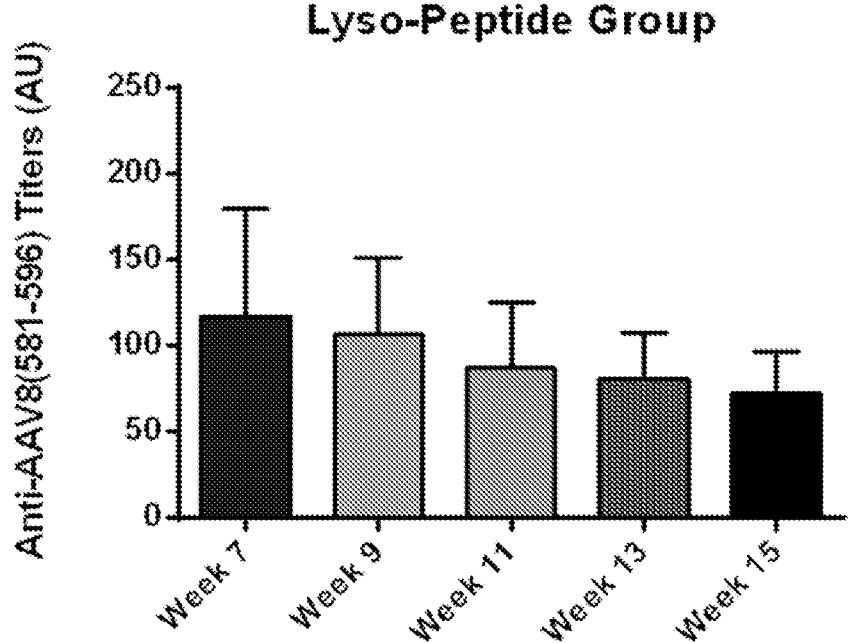
FIG. 4: Anti AAV8 peptide specific antibody titers after oral gavage.
Figure 4:
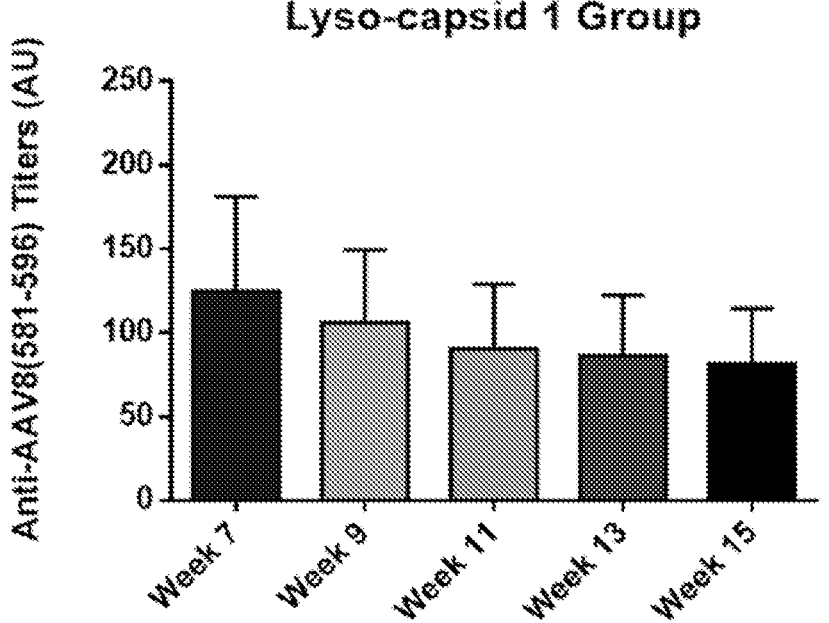

Orally Administered Lyso-PS-AAV8 Capsid and Lyso-PS-AAV8$_{581-596}$ Peptide Nanoparticles have the Potential to Reverse Pre-Existing Anti-AAV8 Antibody Titers Mice were divided into two groups, Group 1 (n=20), receiving 1 µg of free AAV8$_{581-596}$ peptide and Group 2 (n=30), receiving 1 µg of free AAV8 capsid protein (FIG. 2). Both the groups were administered their respective proteins via subcutaneous route for 6 consecutive weeks to achieve comparable sufficiently high anti-AAV8 antibody titers (FIG. 3). Outliers were excluded from the study at sixth week. 16 animals from group 1 and 24 animals from group 2 were chosen for the reversal study following subcutaneous titer induction. The 16 animals chosen from Group-1 at the end of subcutaneous antibody titer induction were divided into 2 treatment groups of 8 animals each (n=8) as depicted in FIG. 2. Whereas, 24 mice selected from Group-2 at the end of subcutaneous induction were further divided into 3 treatment groups. Weekly blood samples were collected via saphenous vein and anti-AAV8 capsid and anti-AAV8 peptide antibody titers were determined at week 7, 9, 11, 13, and 15 of oral gavage. The anti-AAV8 capsid specific antibody titers are depicted in FIG. 3, comparing week 6 (after titer induction) and week 11 (following 5 oral treatments) for Lyso-PS-AAV8 capsid group. Before oral gavage treatment, Week 6, the mean antibody titer level was −130 AU. On week 11, following 5 weeks of oral treatment, a clear reduction in the anti-AAV8 titer was observed. Similar comparison for animals treated with free AAV8 showed an increase in titer levels between week 6 and 11 whereas buffer treated group was comparable. This observation demonstrated that oral treatment of Lyso-PS-AAV8 capsid reversed the pre-existing antibody against AAV8 capsid. As the oral treatment progress, similar trend continue for treatment groups. The anti-AAV8$_{581-596}$ peptide titer levels are represented in the form of bar graphs from week 7 through the end of the treatment, week 15 in FIG. 4. Lyso-peptide treatment group also showed similar results. There was a clear trend of reduction in the AAV8$_{581-596}$ peptide specific titers in the 2 treatment groups "lyso-peptide" and "lyso-capsid 1" at the end of 9-week oral treatment.

Example 2

The following provides description of use of liposomes and liposome complexes of the present disclosure.

Adenovirus (Ad) is a non-enveloped, linear double-stranded DNA virus with 57 identified human Ad serotypes. Ad serotypes differ in tropism and further divided into six subgroups, A-G. Different in subgroup represent different serotypes. The viral capsid is comprised of capsid proteins, core proteins, and cement proteins. The adenovirus virion has unique viral structure: 90-100 nm in size, non-enveloped, icosahedral particle containing a nucleocapsid. The viral capsid consists of 252 proteins, involving three distinct types: fiber, penton, and hexon based proteins. There are 240 hexon proteins and 12 penton proteins. Each hexon capsomere is a homotrimer of the hexon protein, a complex protein of around 900 residues. Each hexon monomer has seven flexible, serotype-specific loops, named hypervariable regions (HVRs) and different serotypes will have minor different in hypervariable regions. Adenovirus hexon 5 protein belongs to subgroup C with a molecular weight of 108 kDa and isoelectric point of 5.15.

Lysops-Ad5 Preparation:

LysoPS lipid nanoparticles were prepared at a molar ratio of 30:70 of LysoPS to DMPC in chloroform. LysoPS lipid nanoparticles were prepared using dehydration and rehydration method. Chloroform solvent was removed by rotary evaporation to form a thin lipid film on the bottom of a test tube and rehydrated in 1 mL of sterile 5 mM citrate buffer at pH 4.5. Lyso-PS lipid nanoparticles were subjected to extrusion through a polycarbonate membrane of 200 nm pore size using high-pressure nitrogen extrusion. The mean diameter of lipid nanoparticles was confirmed by dynamic light scattering (Nicomp 380 Particle Sizer, Particle Sizing System, Port Richey, Florida). Lipid concentration was determined by phosphate assay. The molar ratio of Ad5-hexon protein (Bio-rad) to lipid used was 1:10,0000. To prepare adenovirus virus 5 hexon protein with lyso-PS lipid nanoparticle (Lyso-Ad5) formation, Lyso-PS lipid nanoparticles were loaded with ad5-hexon protein using a trigger-loading mechanism by incubating hexon protein with LysoPS lipid solution at 37° C. for 30 min (minutes) for association.—

Biophysical Characterization:

Lyso-PS-Ad5 complexes were prepared as described above and separated using ultracentrifugation at 60000 RCF for 1 hour at 4 C. Associated Lyso-PS-Ad5 will form a pellet and unassociated hexon protein will be in the supernatant. Lyso-PS-Ad5 were collected and digested with 1% Tween 20 to disrupt LysoPS bilayer and incubated at 37° C. for 15 min. Samples were quantified using micro-bca assay The association efficiency were calculated using the formula $$\frac{Lyso-PS-Ad5 - Free\ Lyso-Ps}{Total\ amount\ of\ Ad5\ hexon\ protein} \times 100\%.$$

Lyso-PS-Ad5 has an association efficiency of 66.1%±5.47%, and particle diameter increased from (98.5 nm±2.55) to (165.8 nm±7.53) after association. See Table 2.

TABLE 2

| Lyso-PS-Ad5 hexon protein association | | Association efficiency |
|---|---|---|
| Trial 1 | | 60.5 |
| Trial 2 | | 71.4 |
| Trial 3 | | 66.3 |
| Average | | 66.1 |
| Standard Error | | 5.4 |

| | | Sizes(nm) | Chi-Sq |
|---|---|---|---|
| Free LysoPS | Trial 1 | 95.6 | 1.08 |
| | Trial 2 | 99.7 | 0.67 |
| | Trial 3 | 100.3 | 0.5 |
| | Average | 98.5 | 0.75 |
| | Standard I | 2.55 | 0.29 |
| LysoPS-Ad5 | Trial 1 | 157.9 | 0.35 |
| | Trial 2 | 166.6 | 4.45 |
| | Trial 3 | 172.9 | 0.34 |
| | Average | 165.8 | 1.71 |
| | Standard I | 7.53 | 2.37 |

Example 3

Figure 5:
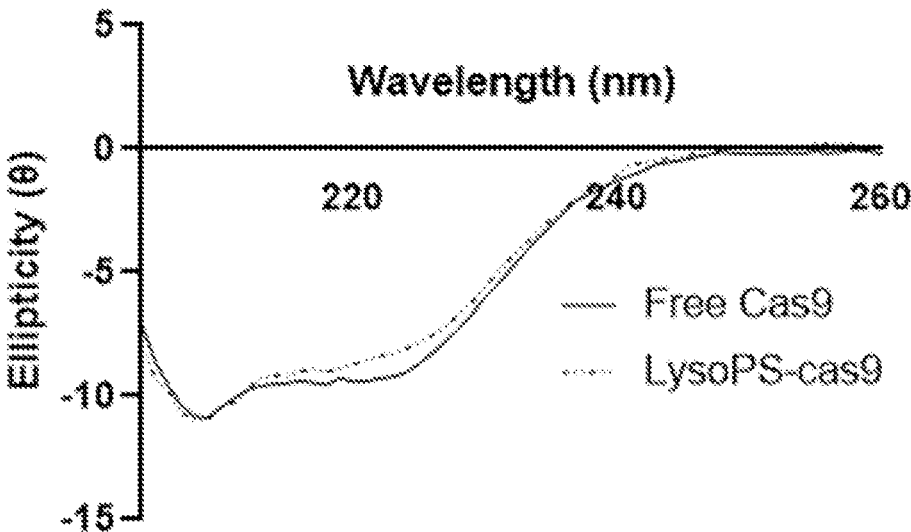
FIG. 5: Far UV CD spectra of Cas9 and LysoPS-Cas9.
Figure 6:
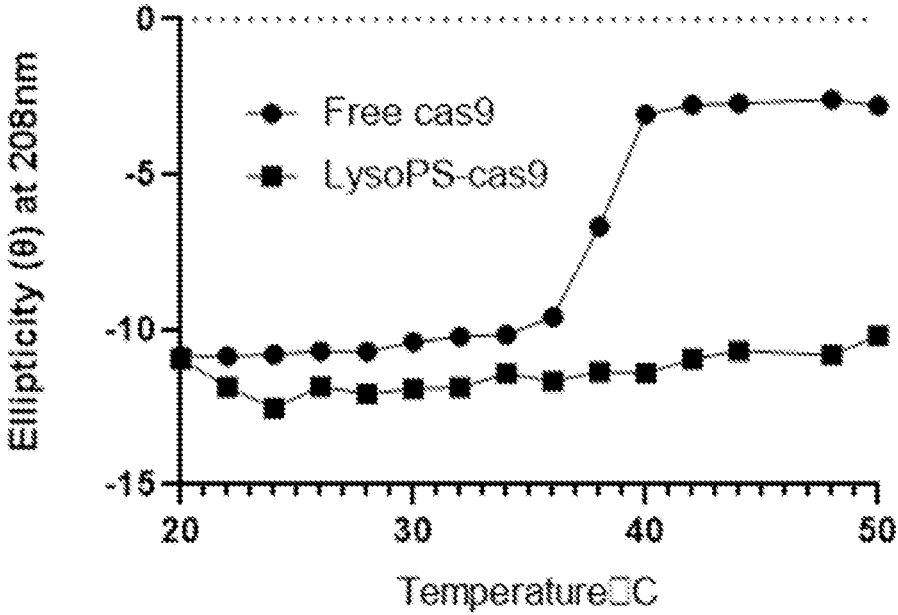
FIG. 6: Unfolding profile of Cas9 and LysoPS Cas9 using Far UV CD spectroscopy.

The following provides description of use of liposomes and liposome complexes of the present disclosure.
Rational Design of Cas9 Associated with Lyso-PS Liposomes:

Cas9 protein was successfully associated with Lyso-PS nanoparticle for CRISPR-based therapy. The conditions were identified based on conformational and folding analysis of Cas9 under stress conditions. Based on these biophysical studies, the association conditions are identified as HEPES buffer, 37° C. for about 40 min. The association efficiency of 42.8±13.5 (mean±SEM) (n=3) with lyso-PS liposomes was achieved. LysoPS nanoparticle diameter increased from 98.7 nm±2.3 to 233.5 nm±43.1 after association. The Lyso-PS-Cas9 complexes were characterized using far-UV circular dichroism (CD) (FIG. 5). These data showed association of Cas9 with Lyso-PS did not alter the secondary structure of Cas9. Further, unfolding studies using far-UV CD was carried out to investigate whether Lyso-PS association alter the stability of the protein (FIG. 6). The spectral analysis showed that the lyso-PS improved stability of Cas9. Cas9 was purchased from Sigma Aldrich (St. Louis, MO).
Reversal of Pre-Existing Cas9 Titers Using Lyso-PS-Cas9 Nanoparticle.

Male Swiss Webster mice were subcutaneously immunized with 1 μg of Cas9 protein (which originated from Streptococcus pyogenes bacteria) weekly for a total of 4 weeks to stimulate and generate anti Cas9 antibody followed by 3 weeks of wash out (without treatment). Host immunity toward Cas9 protein was measured via anti-Cas9 antibodies ELISA.

Figure 7:
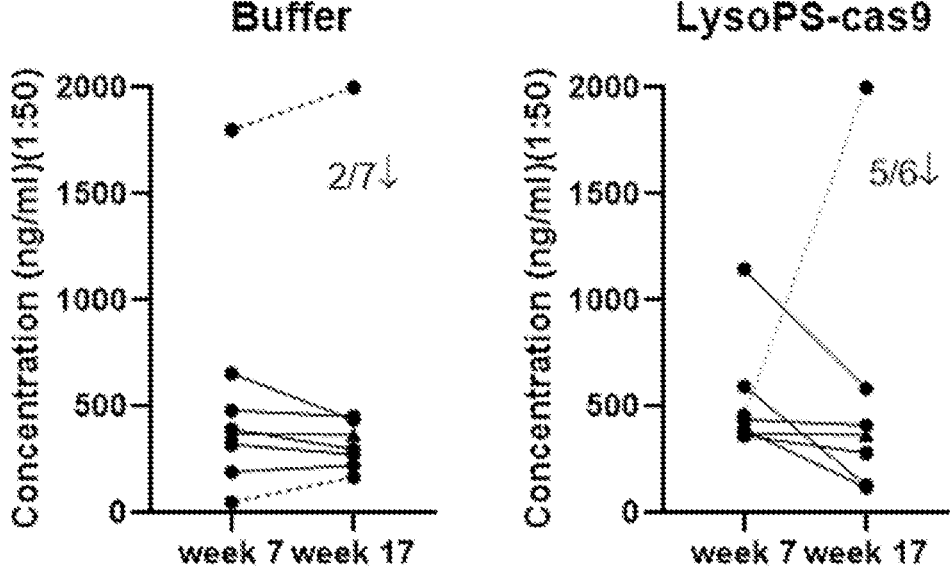
FIG. 7: Comparison of anti-cas9 antibodies titers between week 7 and week 17 in treatment groups. Each individual sample were labeled as solid circle and a positive control sample, a mouse plasma sample were induced with cas9 for 3 weeks but without any treatment were added as internal control, labeled as solid triangle. Samples with dash line illustrate an increase in anti-Cas9 antibody and the number on the graph represent the number of animals reduced in antibodies titers. Concentration of cas9 antibodies were presented in ng/ml using a standard antibody and presented concentration in 50-fold dilution.

Mice were divided into groups according to anti-Cas9 antibodies titers with comparable titers between buffer and lyso-PS-Cas9 complex treatment groups. The oral administration was initiated on week 7 with 100 μL of 200 mM HEPES buffer or Lyso-PS-Cas9 complex. In LysoPS-Cas9 complex group, 1 μg of protein were used to formulate Cas9 containing Lyso-PS lipid nanoparticles with a protein-lipid ratio of 1:10,000 and trigger loaded Cas9 into nanoparticle by incubating at 37° C. for 30 min in 200 mM HEPES buffer at pH 7.4. These data showed mice that received Lyso-PS-Cas9 complex showed a reduction in anti-Cas9 antibodies titers where 5 out of 6 animals showed a reduction in titers, while one animal showed an increase (FIG. 7) possibly due to a wound that was visible. The treatment group that received HEPES buffer showed that only 2 out of 7 mice showed a reduction in anti-Cas9 antibodies titers.

Example 4

The following provides description of use of liposomes and liposome complexes of the present disclosure.
Rational Design of AAV5 Associated with Lyso-PS Liposomes Lyso-PS liposomes were formulated in PBS with 1 mM CaCl₂) at pH 6. Liposomes were then incubated with AAV5 at a protein lipid ratio of 1:10,000 at 45° C. for 30 min. Free and associated protein were separated by ultracentrifugation, spun at 60,000 g, causing liposomes to pellet while allowing free AAV5 to remain in the supernatant. After spinning, pellets were rehydrated in 300 μL of buffer and assayed for protein amount by microBCA assay. Amounts obtained from the BCA were compared to initial amount of protein added to ultracentrifuge. It was found that 43.2% of the AAV5 was associated under these conditions. The complexes were analyzed and sized by Dynamic Light Scattering (DLS). Liposomes prior to association had a size of 121.8 nm (SD=1) and increased to 220.9 nm (SD=9.8 nm) when associated to AAV5.

TABLE 3

| Trial | Free Liposome size | Associated Liposome size | % association |
|---|---|---|---|
| 1 | 122.8 | 211.1 | 43.5 |
| 2 | 120.8 | 230.7 | 42.9 |
| Average | 121.8 | 220.9 | 43.2 |
| SD | 1 | 9.8 | 0.32 |

Example 5

The following provides description of use of liposomes and liposome complexes of the present disclosure.

A reversal study was performed in mice using Lyso-PS-AAV8.

First anti-AAV8 titers were induced by giving all mice 5e9VP/mouse AAV8, subcutaneously, formulated in endotoxin free PBS pH=7.28. All mice received 7 weekly subcutaneous induction doses. Titers were analyzed using an in-house developed anti-AAV8 ELISA assay and mice were separated into 3 groups (n=16) with similar mean titers and titer distribution. Treatment groups consisted of buffer alone, LysoPS liposomes alone, or Lyso-PS associated with AAV8 (Lyso-PS-AAV8). Preformed Lyso-PS liposomes were able to associate with AAV8 particles via incubation in citrate buffer pH=4.5 at 37° C. for 30 min. Starting on week 10, mice received weekly oral gavage treatments for 10 weeks with blood sampled via saphenous vein every 2 weeks to monitor titers. Oral gavage dose for Lyso-PS-AAV8 was 2.5e9VP/mouse with approximately 0.0177 µmol/mouse Lyso-PS liposomes. 2 weeks following the final oral gavage treatment half the mice from each group (n=8) were sacrificed and spleens and mesenteric lymph nodes (MLNs) were collected. Samples were stained and fixed and flow cytometry was done the following day. The other half of animals in each groups (n=8) were challenged IV with 5e9VP/mouse free AAV8 to simulate receiving an IV gene therapy. These mice were sacrificed 2 weeks following IV challenge and spleens and MLNs were collected to run on the flow cytometer the following day.

Figure 8:
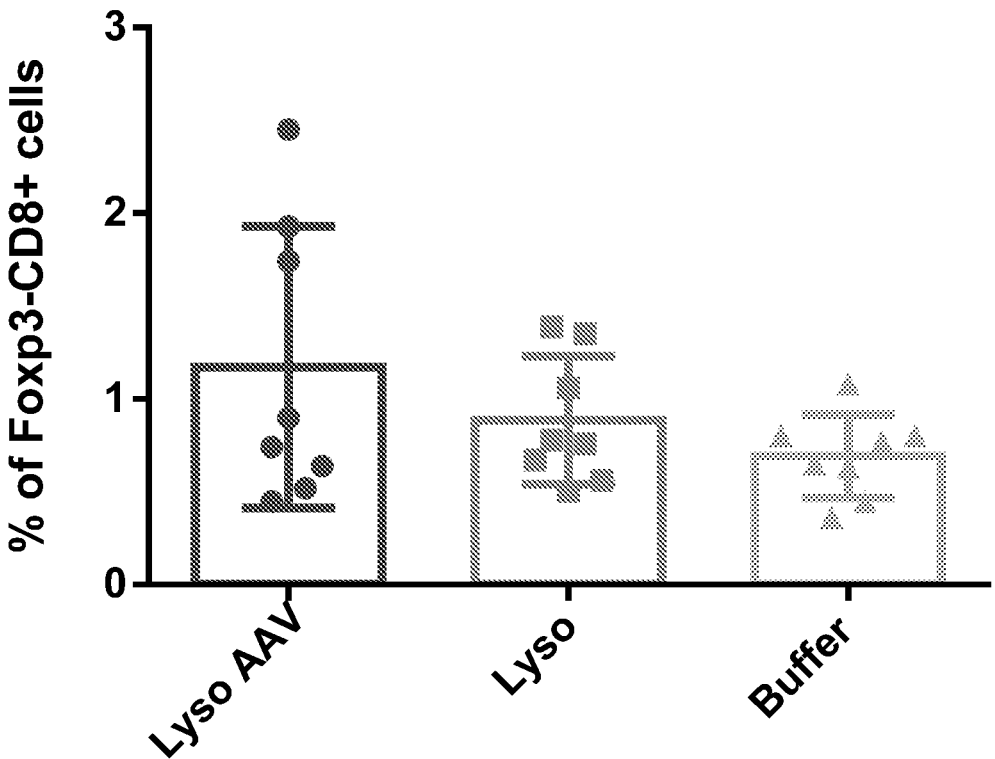
FIG. 8: Elevated levels of LAG3+CD49b+CD8+ Cells were found in the spleen of LysoPS-AAV8 fed animals after oral administration.

Data from these experiments are shown in FIG. 8.

Example 6

The following provides description of use of liposomes and liposome complexes of the present disclosure.

TABLE 4

| Normalized Absorbance @ 1:20 Dilution | 1101 | 1102 | 1103 |
| --- | --- | --- | --- |
| Pre Study | 1 | 1 | 1 |
| Day 15 | 0.941 | 0.757 | 0.985 |
| Day 29 | 0.871 | 0.757 | 0.914 |
| Day 43 | 0.661 | 0.689 | 0.885 |

A transient increase in LAP+ Tregs was found in the peripheral blood of primates at Day 29 which reduced back near baseline within 2 weeks (day 43). Unstained and FMO control values for LAP+ Tregs were 1.24% and 1.72% respectively.

TABLE 5

| LAP+ Tregs (% of CD4 cells) | 1101 | 1102 | 1103 |
| --- | --- | --- | --- |
| Pre-Study | 0.74 | 1.6 | 0.52 |
| Day 29 | 5.04 | 3.99 | 1.33 |
| Day 43 | 1.42 | 0.68 | 0.96 |

The preceding description provides specific examples of the present invention. Those skilled in the art will recognize that routine modifications to these embodiments can be made which are intended to be within the scope of the description.

```
                        SEQUENCE LISTING

<160> NUMBER OF SEQ ID NOS: 1

<210> SEQ ID NO 1
<211> LENGTH: 15
<212> TYPE: PRT
<213> ORGANISM: Homo sapiens

<400> SEQUENCE: 1

Ile Val Ala Asp Asn Leu Gln Gln Asn Thr Ala Pro Gln Ile Gly
1               5                   10                  15
```

A reversal study was performed in primates using Lyso-PS-AAV8.

A total of 3 cynomolgus macaques were used in this study. Blood and plasma samples were taken the day prior to the study start to have baseline values to compare with post treatment. All animals used in the study had greater than 1:20 neutralizing antibodies prior to receiving treatment. All 3 primates received 4 weekly oral gavage treatments of Lyso-PS-AAV8. Preformed LysoPS liposomes were able to associate with AAV8 particles via incubation in citrate buffer pH=4.5 at 37° C. for 30 min. Primates were dosed at 2.66e10VP/kg on day 1. Mean size and Chi squared values were monitored for all formulations to ensure batch to batch consistency. Animals were bled weekly for sample measurements. Endpoints included AAV8 neutralizing antibody assessment, total anti-AAV8 titer analysis, blood and serum chemistry, peripheral blood cytokine levels via multiplex assay, and PBMC phenotyping via flow cytometry. The formulation was found to be well tolerated with no abnormal blood and serum chemistry observed. During this short oral immunization regimen, neutralizing antibodies remained above 1:20 for the entire study, but total anti-AAV8 antibodies were reduced when assessed at 1:20 dilution via an in-house made ELISA assay.'

The invention claimed is:

1. A method of reducing generation of antibodies against a viral vector protein comprising administering to an individual in need of treatment a composition comprising liposomes, wherein the liposomes comprise phosphatidylcholine (PC) and lysophosphatidylserine (lyso-PS), wherein the ratio of PC to lyso-PS is from 90:10 to 60:40, wherein some or all of the PS is present as lyso-PS and wherein the liposomes are complexed to the viral vector protein or an antigenic fragment thereof, wherein the viral vector protein or antigenic fragment thereof comprises the sequence (SEQ ID NO: 1)
IVADNLQQNTAPQIG.

2. The method of claim 1, wherein the acyl chain of the lyso-PS is oleic acid.

3. The method of claim 1, wherein all of the PS is present as lyso-PS.

4. The method of claim 1, wherein the ratio of PC to lyso-PS is from 85:15 to 70:30.

5. The method of claim 1, wherein the PC is present as dimyristoyl-sn-glycero-3 phosphatidylcholine (DMPC).

\* \* \* \* \*